(12) United States Patent
Hasegawa et al.

(10) Patent No.: US 10,859,686 B2
(45) Date of Patent: Dec. 8, 2020

(54) OUTER CASE FOR ULTRASONIC PROBE

(71) Applicant: NIHON DEMPA KOGYO CO., LTD., Tokyo (JP)

(72) Inventors: Yasunobu Hasegawa, Saitama (JP); Kazuhiko Komiyama, Saitama (JP)

(73) Assignee: NIHON DEMPA KOGYO CO., LTD., Tokyo (JP)

( * ) Notice: Subject to any disclaimer, the term of this patent is extended or adjusted under 35 U.S.C. 154(b) by 317 days.

(21) Appl. No.: 16/136,289

(22) Filed: Sep. 20, 2018

(65) Prior Publication Data
US 2019/0094348 A1 Mar. 28, 2019

(30) Foreign Application Priority Data
Sep. 28, 2017 (JP) ................. 2017-187382

(51) Int. Cl.
*G01S 7/52* (2006.01)
*H05K 5/00* (2006.01)
*H05K 5/02* (2006.01)
*A61B 8/00* (2006.01)

(52) U.S. Cl.
CPC ........... *G01S 7/52084* (2013.01); *A61B 8/44* (2013.01); *G01S 7/52079* (2013.01); *H05K 5/0013* (2013.01); *H05K 5/023* (2013.01); *H05K 5/0247* (2013.01)

(58) Field of Classification Search
CPC ... G01S 7/52084; G01S 7/52079; A61B 8/44; A61B 8/4444; H05K 5/023; H05K 5/0013; H05K 5/0247
See application file for complete search history.

(56) References Cited

U.S. PATENT DOCUMENTS

| D847,353 S | * | 4/2019 | Hasegawa | ................. D24/187 |
| 2019/0094348 A1 | * | 3/2019 | Hasegawa | ............ H05K 5/0013 |
| 2019/0094349 A1 | * | 3/2019 | Hasegawa | ............ G01S 7/52079 |

FOREIGN PATENT DOCUMENTS

| CN | 109567857 A | * | 4/2019 | ............. H05K 5/023 |
| CN | 109567858 A | * | 4/2019 | ........ G01S 7/52084 |
| JP | 2004008372 A | * | 1/2004 | ............. A61B 8/546 |
| JP | 2008000855 | | 1/2008 | |
| JP | 2011050694 | | 3/2011 | |
| JP | 2012034877 | | 2/2012 | |
| JP | 2019058562 A | * | 4/2019 | ........ G01S 7/52084 |
| JP | 2019058563 A | * | 4/2019 | ........ G01S 7/52079 |

OTHER PUBLICATIONS

Translation of JP2004008372 (Year: 2004).*

* cited by examiner

*Primary Examiner* — Daniel Pihulic
(74) *Attorney, Agent, or Firm* — JCIPRNET

(57) ABSTRACT

An outer case for an ultrasonic probe that houses a module of the ultrasonic probe is provided. The outer case includes a grip case gripped by a user and a head case that engages with the grip case. The grip case has a first engaging portion where one or a plurality of convex portions are disposed. The head case has a second engaging portion where one or a plurality of depressed portions are disposed at positions where the one or plurality of depressed portions engage with the one or plurality of convex portions. The convex portion and the depressed portion are engaged to be locked.

5 Claims, 9 Drawing Sheets

OUTER CASE FOR ULTRASONIC PROBE

CROSS-REFERENCE TO RELATED APPLICATIONS

This application is based on and claims priority under 35 U.S.C. § 119 to Japanese Patent Application No. 2017-187382, filed on Sep. 28, 2017, the entire content of which is incorporated herein by reference.

TECHNICAL FIELD

This disclosure relates to an outer case for an ultrasonic probe that houses a module of the ultrasonic probe.

DESCRIPTION OF THE RELATED ART

An ultrasonic probe (a transducer) is a sensor in which a crystal unit (a piezoelectric element) that transmits and receives an ultrasonic sound wave is embedded. The ultrasonic probe is used in usages, such as medical diagnosis, health care, and non-destructive inspection. The ultrasonic probe includes components, such as the crystal unit (the piezoelectric element), a backing material, an acoustic matching layer, an acoustic lens, and a case that houses these components.

The case for the ultrasonic probe includes a case separated into a grip case gripped by an operator (a user) and a head case housing a unit, such as the crystal unit. In the case of such a case, the grip case and the head case are fixed with, for example, an adhesive. The case for the ultrasonic probe includes a case whose grip case and head case are configured to be attachable/removable (see Japanese Unexamined Patent Application Publication No. 2012-34877).

As described above, when the grip case and the head case are fixed with, for example, an adhesive, a level difference could occur at a seam (a joint) of the cases due to an adhesion slip and an adhesive portion of the cases is easily peeled off by, for example, an impact. In the case of the case described in Japanese Unexamined Patent Application Publication No. 2012-34877, there is a level difference at a seam of the cases and the cases are peeled off only by an operator pushing a flexible member in; therefore, there is a risk that the operator accidentally detaches the case.

A need thus exists for an outer case for an ultrasonic probe which is not susceptible to the drawback mentioned above.

SUMMARY

According to an aspect of this disclosure, there is provided an outer case for an ultrasonic probe that houses a module of the ultrasonic probe. The outer case includes a grip case gripped by a user and a head case that engages with the grip case. The grip case has a first engaging portion where one or a plurality of convex portions are disposed. The head case has a second engaging portion where one or a plurality of depressed portions are disposed at positions where the one or plurality of depressed portions engage with the one or plurality of convex portions. The convex portion and the depressed portion are engaged to be locked.

BRIEF DESCRIPTION OF THE DRAWINGS

The foregoing and additional features and characteristics of this disclosure will become more apparent from the following detailed description considered with reference to the accompanying drawings, wherein.

DETAILED DESCRIPTION

Figure 1A:
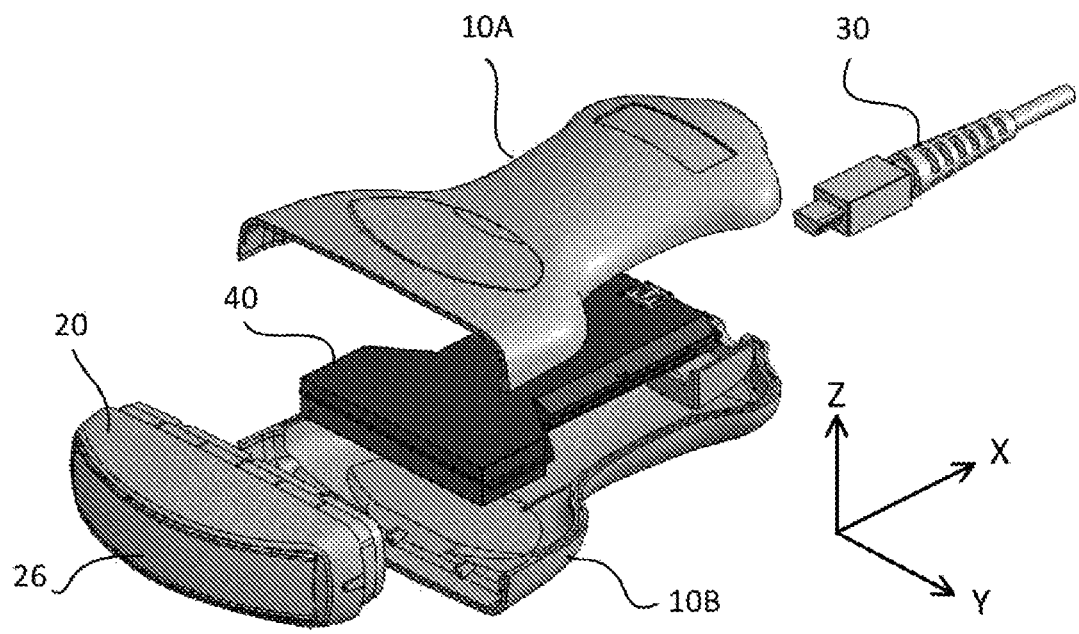
FIG. 1A and FIG. 1B are perspective views illustrating a configuration of an ultrasonic probe according to an embodiment.

The following describes an embodiment of this disclosure with reference to the drawings. It will be understood that the scope of the disclosure is not limited to the described embodiment. A scale of an expressed drawing may be adjusted to explain the embodiment. For example, a part of a drawing is enlarged or stressed as required when it is described.

Each of the following drawings uses an XYZ coordinate system to describe directions in the drawings. In this XYZ coordinate system, a longitudinal direction of an ultrasonic probe is assumed to be an X-direction (an X-axis) and a plane perpendicular to the X-axis is assumed to be a YZ-plane. On this YZ-plane, a longitudinal direction of a cross-sectional surface (a cross-sectional surface of a base plate described later) of the ultrasonic probe is indicated as a Y-direction (a Y-axis) and a short side direction of the cross-sectional surface of the ultrasonic probe is indicated as a Z-direction (a Z-axis). It is described that directions pointed by arrows in the drawings are assumed to be + directions of each of the X, Y, and Z-directions. The directions opposite of the arrow directions are assumed to be − directions.

Figure 1B:
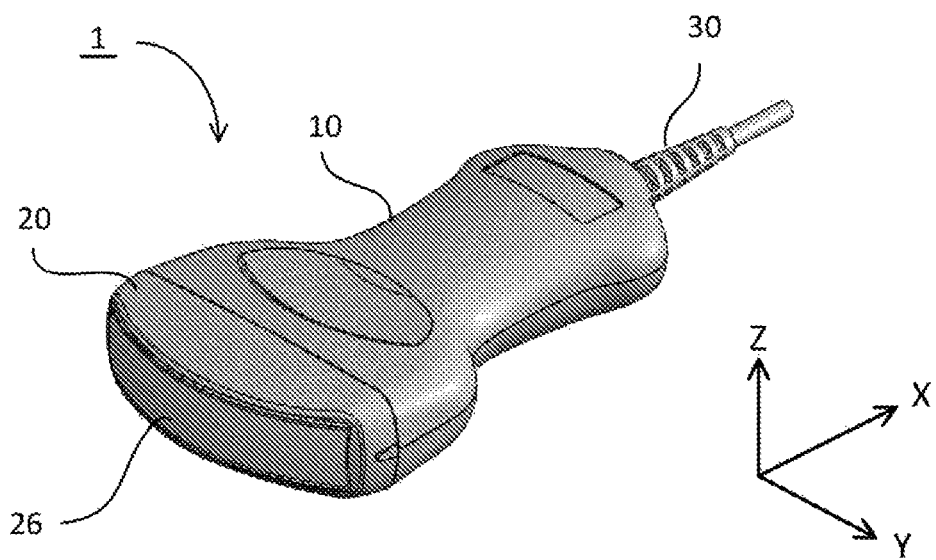

FIG. 1A and FIG. 1B are perspective views illustrating a configuration of an ultrasonic probe 1 (an ultrasonic transducer) according to an embodiment. FIG. 1A is an exploded perspective view illustrating each part constituting the ultrasonic probe 1, and FIG. 1B is a completion perspective view illustrating a state where each part constituting the ultrasonic probe 1 is assembled. Note that FIG. 1A and FIG. 1B illustrate a convex type probe as an example of the ultrasonic probe 1. As illustrated in FIG. 1B, the ultrasonic probe 1 includes a grip case 10, a head case 20, a USB cable 30, and a base plate 40.

The grip case 10 is an internally hollow case gripped by an operator (a user) of the ultrasonic probe 1. As illustrated in FIG. 1A, the grip case 10 is configured by combining two parts, that is, a first grip case 10A and a second grip case 10B. As illustrated in FIG. 1A, the base plate 40 is housed inside the grip case 10. The grip case 10 has a cross-sectional surface (the YZ-plane) in a flat elliptical shape (a rectangular shape with four rounded corners). The grip case 10 has a depressed central portion in the X-direction (a constriction is disposed in the central portion in the X-direction of the grip case 10) such that the operator can easily hold. A −X-direction of the grip case 10 is opened and a hole (see a hole 13c in FIG. 2 and FIG. 3B) is formed in a +X-direction of the grip case 10.

The head case 20 is an internally hollow case in which a unit (a module that transmits and receives an ultrasonic sound) constituted of, for example, a crystal unit (a piezoelectric element), which is not illustrated, a backing material, and an acoustic matching layer is housed. This head case 20 has a cross-sectional surface (the YZ-plane) in a flat elliptical shape (a rectangular shape with four rounded corners). A +X-direction of the head case 20 is opened and the opening of the head case 20 and the opening of the grip case 10 are engaged. In a −X-direction of the head case 20, an acoustic lens 26 is attached. Note that the piezoelectric element is a component that generates an ultrasonic sound wave. The backing material is a member that is put in after the piezoelectric element in order to reduce an extra vibration of the piezoelectric element. The acoustic matching layer is a medium material that is disposed between the piezoelectric element and a photographic subject and matches their acoustic impedance. The acoustic lens 26 is a portion like a gray colored rubber disposed at an end of the ultrasonic probe 1 and is a component that focuses the ultrasonic sound wave in a predetermined direction to improve a resolution.

The USB cable 30 (Universal Serial Bus) is a cable for connecting the ultrasonic probe 1 to an information equipment, such as a computer. The base plate 40 is equipped with a transmitting and receiving module that transmits and receives data between the unit of the ultrasonic probe 1 and the information equipment.

As illustrated in FIG. 1A, a procedure for assembling the ultrasonic probe 1 is as follows. The base plate 40 is housed inside the second grip case 10B (or the first grip case 10A) and then, peripheral edge portions (see an edge portion 13 in FIG. 2 and FIG. 3B) of the first grip case 10A and the second grip case 10B are adhered (fixed) with, for example, an adhesive. Then, the unit (the module) is housed inside the head case 20, and the grip case 10 and the head case 20 are engaged in a state where the acoustic lens 26 is attached to the head case 20. Thus, the case of the ultrasonic probe 1 is constituted of three parts of the first grip case 10A, the second grip case 10B, and the head case 20.

Figure 2:
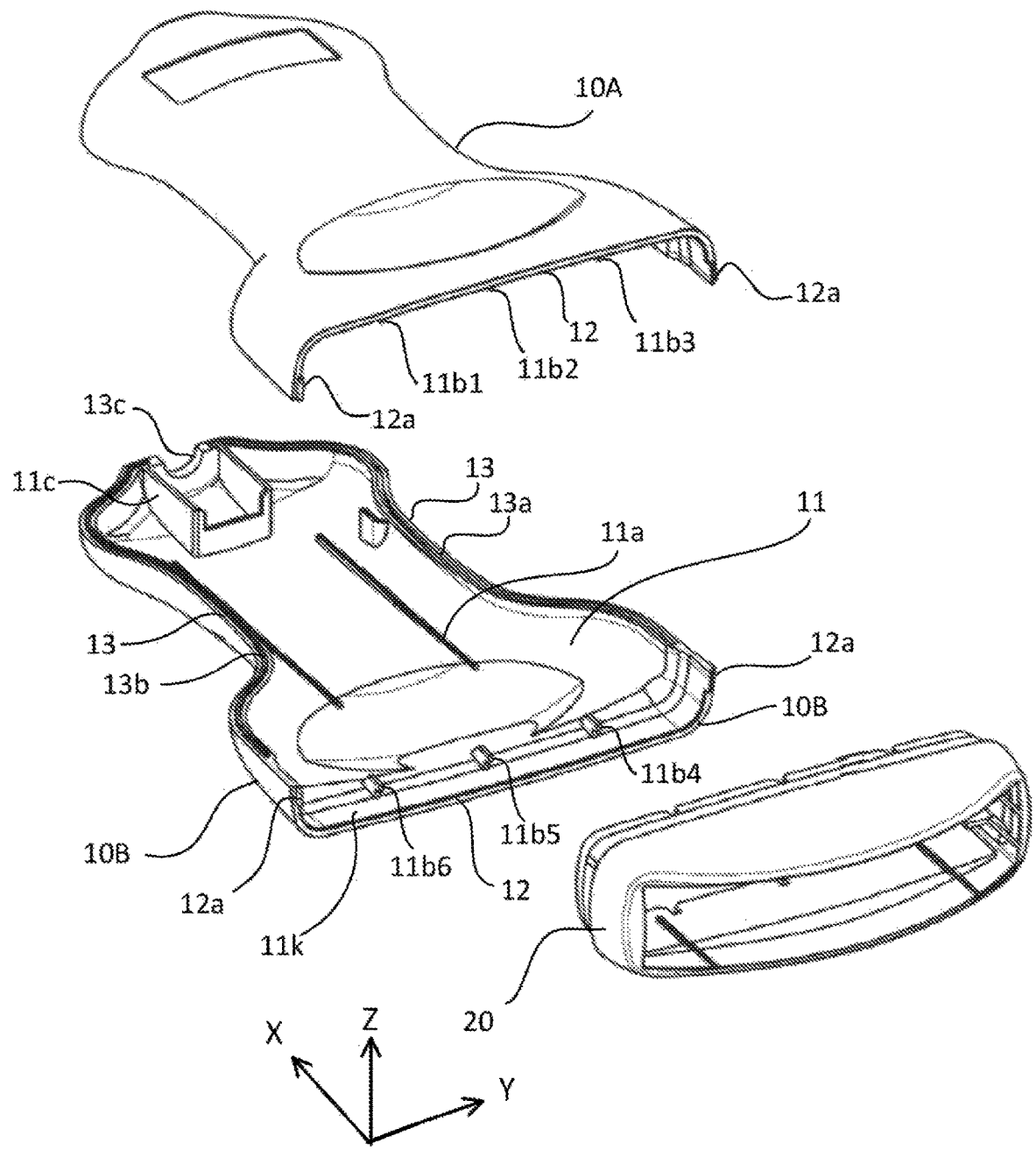
FIG. 2 is a perspective view illustrating each part of a grip case.
Figures 3A, 3B:
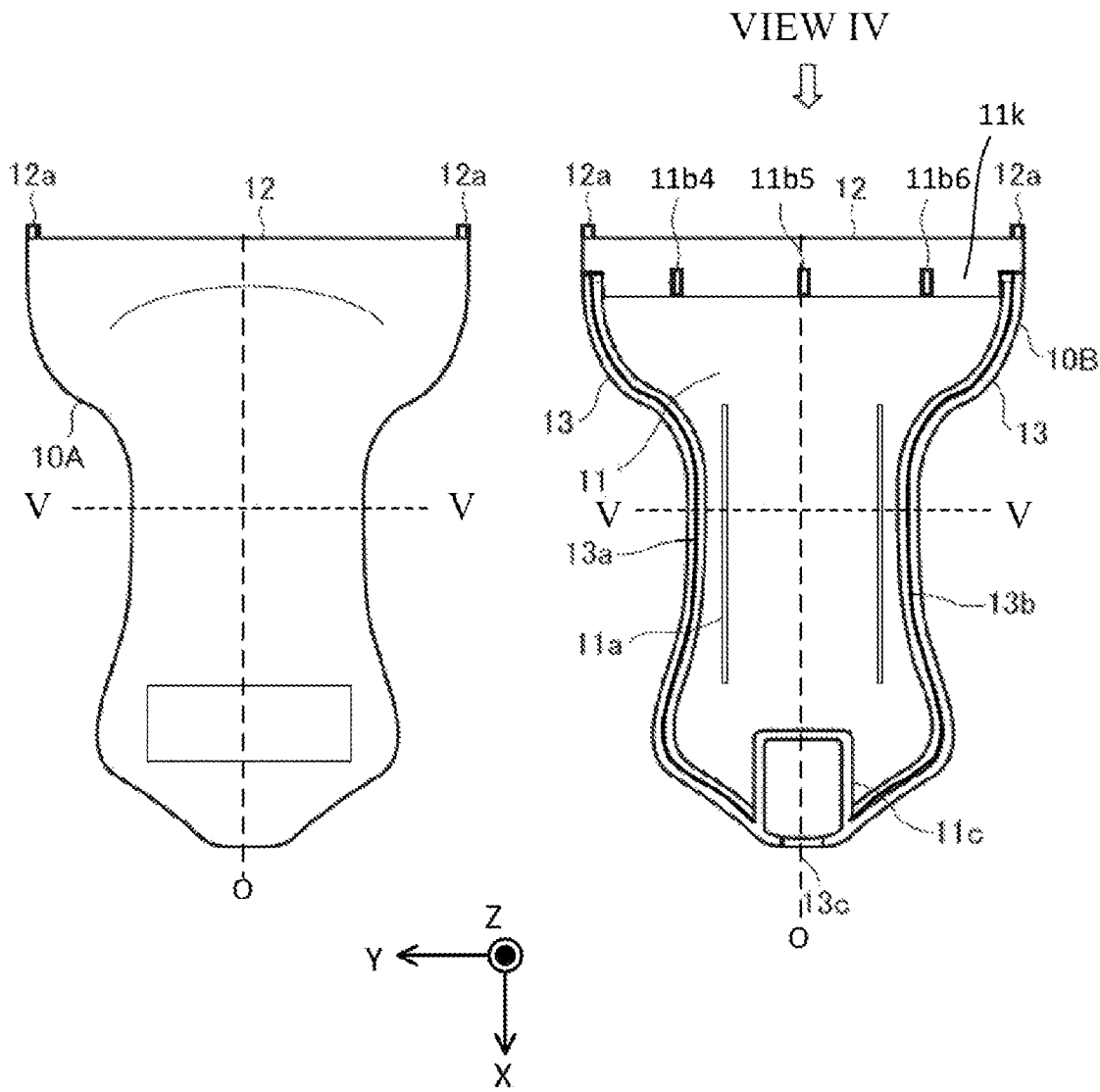
FIG. 3A and FIG. 3B are plan views illustrating each part of the grip case.
Figure 4:
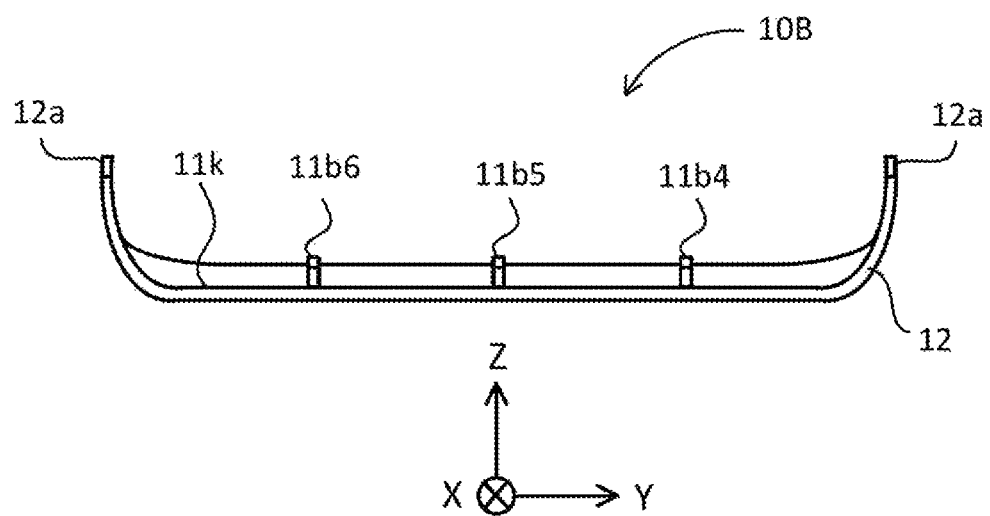
FIG. 4 is a view on an arrow IV of the grip case in FIG. 3B.

FIG. 2 is a perspective view illustrating each part (the first grip case 10A and the second grip case 10B) of the grip case. Noted that, in FIG. 2, not only the grip case 10 is illustrated but the head case 20 is also illustrated. FIG. 3A and FIG. 3B are plan views illustrating each part (the first grip case 10A and the second grip case 10B) of the grip case 10. FIG. 3A is a drawing illustrating an appearance of the first grip case 10A, and FIG. 3B is a drawing illustrating an inside 11 of the second grip case 10B. FIG. 4 is a view on an arrow IV of the grip case (the second grip case 10B) in FIG. 3B. In this embodiment, the first grip case 10A and the second grip case 10B are identical parts (parts with identical shapes and identical sizes).

As illustrated in FIG. 2, FIG. 3A and FIG. 3B, a placement portion 11a for placing the base plate 40 is formed in the inside 11 of the first grip case 10A and the second grip case 10B. As illustrated in FIG. 2, FIG. 3A, FIG. 3B and FIG. 4, an engaging portion 11k that engages with the head case 20 is formed in an opening side (an end portion in the −X-direction) of the inside 11 of the first grip case 10A and the second grip case 10B. As illustrated in FIG. 2, three ribs 11b1, 11b2, and 11b3 are disposed at the engaging portion 11k of the first grip case 10A. Three ribs 11b4, 11b5, and 11b6 are disposed at the engaging portion 11k of the second grip case 10B. Thus, six ribs 11b1 to 11b6 are disposed at the grip case 10 (the first grip case 10A and the second grip case 10B). These six ribs 11b1 to 11b6 constitute convex portions that engage with depressed portions (see cutout portions 22a to 22f illustrated in FIG. 6) of the head case 20.

The rib 11b1 is disposed between a center O and the end portion in the −Y-direction of the peripheral edge portion 12 of the first grip case 10A, and the center O is disposed between both ends (an end portion in a +Y-direction and an end portion in a −Y-direction) of a peripheral edge portion 12 of the first grip case 10A. The rib 11b2 is disposed at the center O between both ends (the end portion in the +Y-direction and the end portion in the −Y-direction) of the peripheral edge portion 12 of the first grip case 10A. The rib 11b3 is disposed between the center O and the end portion in the +Y-direction of the peripheral edge portion 12 of the first grip case 10A, and the center O is disposed between both ends (the end portion in the +Y-direction and the end portion in the −Y-direction) of the peripheral edge portion 12 of the first grip case 10A. The rib 11b4 is disposed between the center O and the end portion in the +Y-direction of the peripheral edge portion 12 of the second grip case 10B, and the center O is disposed between both ends (an end portion in the +Y-direction and an end portion in the −Y-direction) of the peripheral edge portion 12 of the second grip case 10B. The rib 11b5 is disposed at the center O between both ends (the end portion in the +Y-direction and the end portion in the −Y-direction) of the peripheral edge portion 12 of the second grip case 10B. The rib 11b6 is disposed between the center O and the end portion in the −Y-direction of the peripheral edge portion 12 of the second grip case 10B, and the center O is disposed between both ends (the end portion in the +Y-direction and the end portion in the −Y-direction) of the peripheral edge portion 12 of the second grip case 10B.

While in an example illustrated in FIG. 2, FIG. 3A and FIG. 3B, the first grip case 10A and the second grip case 10B each include three ribs, but one, two, and four or more ribs may be disposed. Note that at least one rib is formed at the center O between both ends of the peripheral edge portion 12 of the opening of the grip cases 10A and 10B or in a proximity of the center. Such a configuration ensures fixing "a position where a level difference easily occurs" (that is, the center O between both ends or the proximity of the center easily opens and is easily depressed) in a state where the grip case 10 and the head case 20 are engaged. The ribs 11b1 to 11b6 are members in a flat plate-shape vertically projecting from a surface of the engaging portion 11k (see FIG. 8A, FIG. 8B, and FIG. 9 described later).

A connector portion 11c into which a connector of the USB cable 30 is inserted is formed in an end portion in the +X-direction of the inside 11 of the first grip case 10A and the second grip case 10B. Protrusions 12a that project from the peripheral edge portion 12 in the −X-direction is formed in both ends of the peripheral edge portion 12 of the opening in the −X-direction of the first grip case 10A and the second grip case 10B. These protrusions 12a engage with grooves 24a and 24b (see FIG. 6 and FIG. 7) of the head case 20.

One side from the center O in an opened surface in a pair of the first grip case 10A and the second grip case 10B has the edge portion 13 where a concave shaped spigot (a groove portion) 13a is formed, and the other side in the opened surface has the edge portion 13 where a convex shaped spigot (a projecting portion) 13b is formed. Here, the spigot means a state where parts in concave and convex shape mesh with one another. A portion where the concave shaped portion and the convex shaped portion are engaged, for example, as in a samurai's pillbox, is expressed as a spigot. The spigot is sometimes expressed as a joint (a general term of a structure joining two portions), a connection (a method to join two woods (members) at a right angle or obliquely, or that portion) or the like. The concave shaped spigot 13a of the first grip case 10A and the convex shaped spigot 13b of the second grip case 10B are engaged, and the convex shaped spigot 13b of the first grip case 10A and the concave shaped spigot 13a of the second grip case 10B are engaged. The hole 13c for inserting the USB cable 30 is formed in the end portion in the +X-direction of the edge portion 13 of the first grip case 10A and the second grip case 10B.

Figure 5:
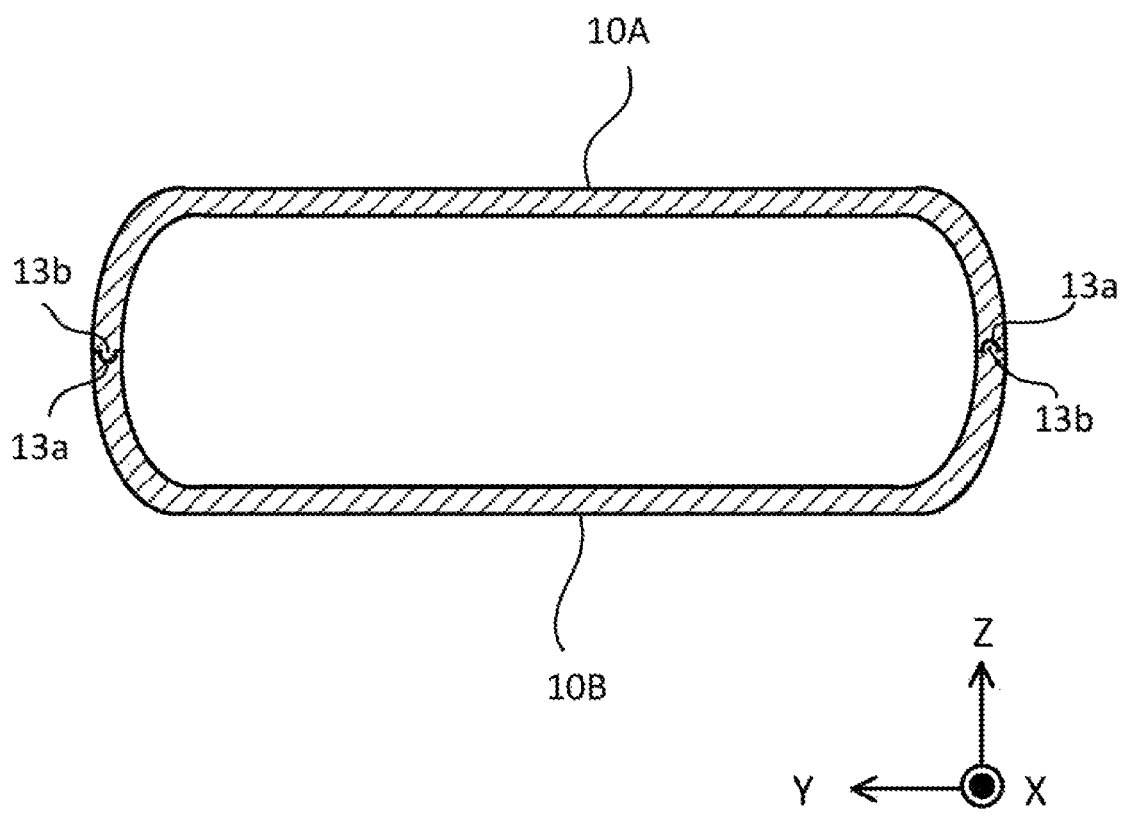
FIG. 5 is a sectional drawing taken along a line V-V of the grip case in FIG. 3A and FIG. 3B.

FIG. 5 is a sectional drawing taken along a line V-V of the grip case 10 in FIG. 3A and FIG. 3B. As illustrated in FIG. 5, the concave shaped spigot 13a of the first grip case 10A and the convex shaped spigot 13b of the second grip case 10B are engaged, and the convex shaped spigot 13b of the first grip case 10A and the concave shaped spigot 13a of the second grip case 10B are engaged. Note that the first grip case 10A and the second grip case 10B are fixedly secured with, for example, an adhesive.

Figure 6:
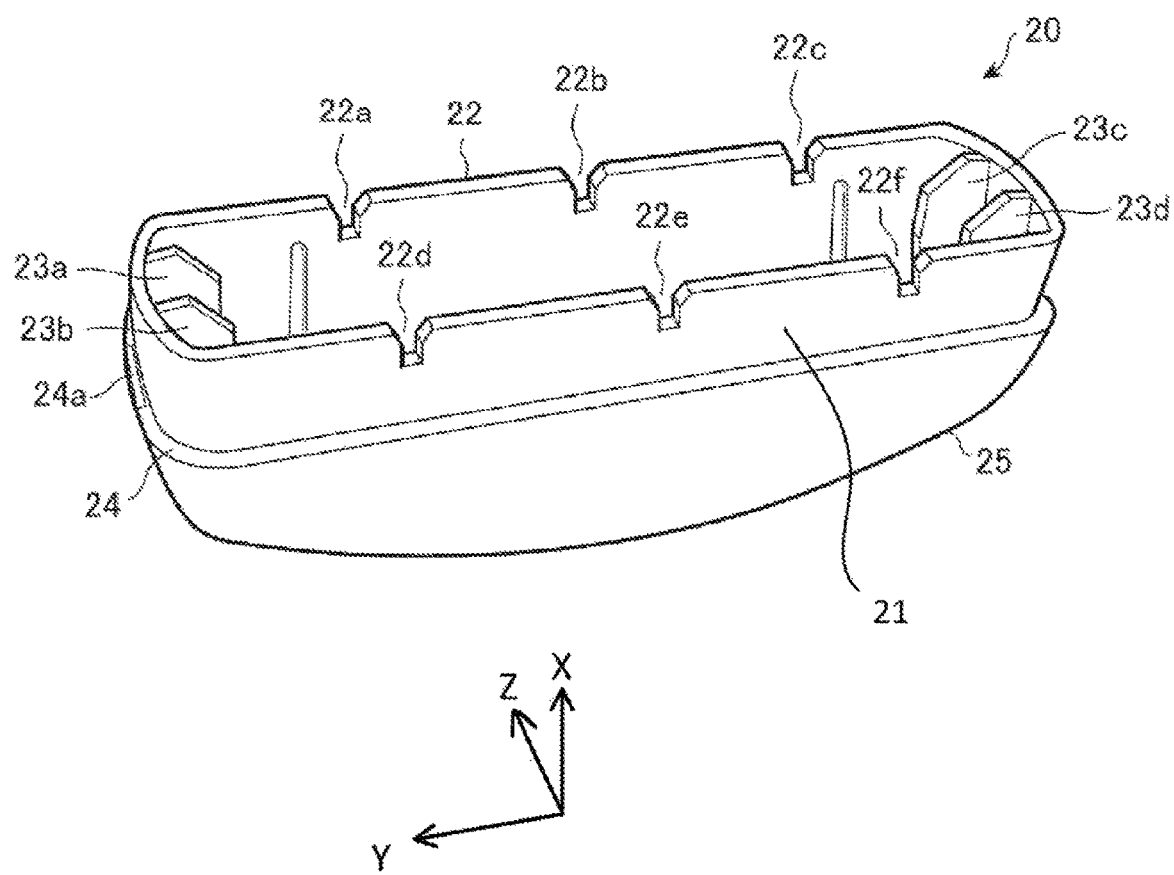
FIG. 6 is a perspective view illustrating a configuration of a head case.
Figure 7:
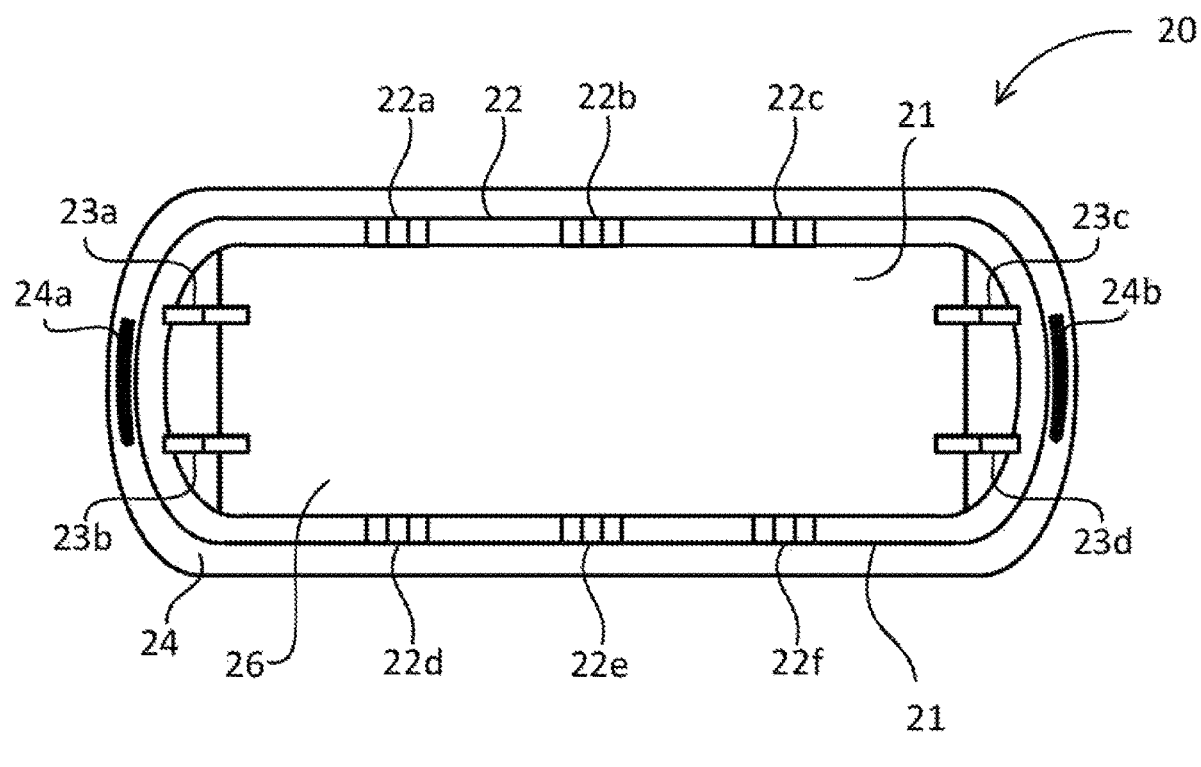
FIG. 7 is a plan view viewed from an opening side of the head case.
Figure 7:
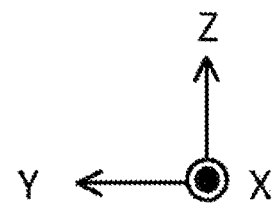

FIG. 6 is a perspective view illustrating a configuration of the head case 20. FIG. 7 is a plan view viewed from an opening side of the head case 20. As illustrated in FIG. 6 and FIG. 7, an engaging portion 21 in a stepped shape that engages with the engaging portion 11k of the opening of the grip case 10 is disposed outside the opening of the head case 20. When the grip case 10 and the head case 20 are engaged, a move in the X-direction is stopped by a step 24 of the engaging portion 21 of the head case 20 contacting the peripheral edge portion 12 of the grip case 10 (the first grip case 10A and the second grip case 10B).

The six cutout portions 22a, 22b, 22c, 22d, 22e, and 22f are formed on the peripheral edge portion 22 of the opening (the engaging portion 21) of the head case 20. The six cutout portions 22a, 22b, 22c, 22d, 22e, and 22f are disposed at respective positions at which the six cutout portions 22a, 22b, 22c, 22d, 22e, and 22f engage with the six ribs 11b1, 11b2, 11b3, 11b4, 11b5, and 11b6 of the engaging portion 11k of the grip case 10 when the grip case 10 and the head case 20 are engaged. That is, in the example illustrated in FIG. 6 and FIG. 7, the cutout portions 22a and 22d are disposed to be opposed at respective positions between a center between both ends (an end portion in the +Y-direction and an end portion in the −Y-direction) of the peripheral edge portion 22 and the end portion in the +Y-direction of the peripheral edge portion 22. The cutout portions 22b and 22e are disposed to be opposed at respective positions in the center between both ends (the end portion in the +Y-direction and the end portion in the −Y-direction) of the peripheral edge portion 22. The cutout portions 22c and 22f are disposed to be opposed at positions between the center between both ends (the end portion in the +Y-direction and the end portion in the −Y-direction) of the peripheral edge portion 22 and the end portion in the −Y-direction of the peripheral edge portion 22. The six cutout portions 22a to 22f constitute depressed portions that engage with the convex portions (the ribs) 11b1 to 11b6 of the grip case 10.

The end portion in the +Y-direction inside the head case 20 includes two stoppers 23a and 23b and the end portion in the −Y-direction inside the head case 20 includes two stoppers 23c and 23d. The stoppers 23a, 23b, 23c, and 23d are portions where the module (the unit) of the ultrasonic probe 1 attached from an outside (the −X-direction side) of a distal end portion 25 of the head case 20 is locked. The stoppers 23a, 23b, 23c, and 23d thus locking the module results in positioning the acoustic lens 26. Both ends of the step 24 include the respective grooves 24a and 24b. These grooves 24a and 24b engage with the protrusions 12a of the grip case 10 when the grip case 10 and the head case 20 are engaged.

Figure 8A:
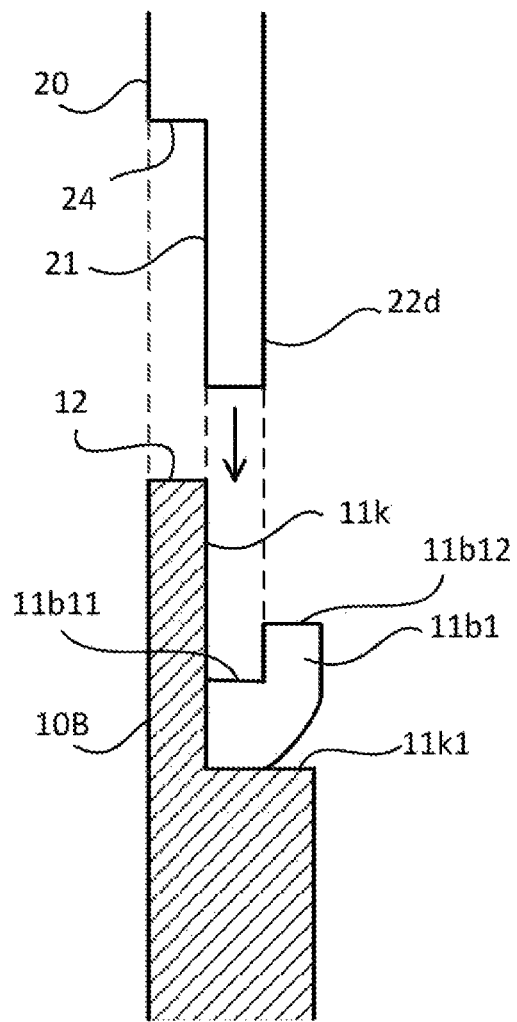
FIG. 8A and FIG. 8B are sectional drawings illustrating a convex portion of the grip case and a depressed portion of the head case.
Figure 8B:
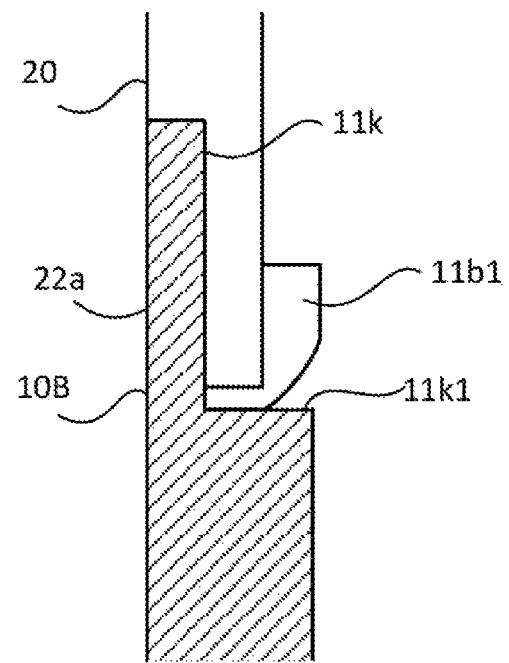
Figure 9:
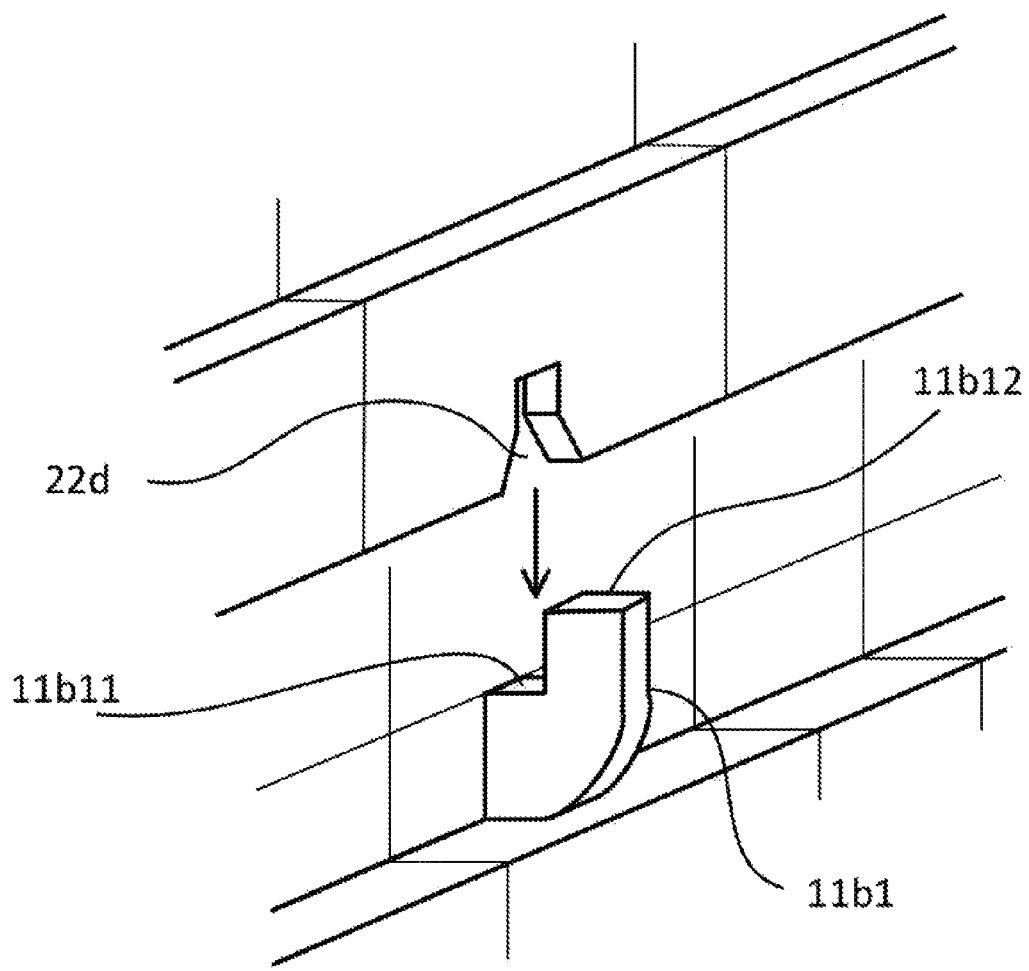
FIG. 9 is a perspective view illustrating the convex portion of the grip case and the depressed portion of the head case.

FIG. 8A and FIG. 8B are sectional drawings illustrating the convex portion (the rib 11b1) of the grip case 10 and the depressed portion (the cutout portion 22d) of the head case 20. FIG. 9 is a perspective view illustrating the convex portion (the rib 11b1) of the grip case 10 and the depressed portion (the cutout portion 22d) of the head case 20. As illustrated in FIG. 8A, FIG. 8B and FIG. 9, the rib 11b1 is formed on a step 11k1 of the engaging portion 11k of the grip case 10 (the first grip case 10A). Upon engagement of the grip case 10 (the first grip case 10A) and the head case 20, the cutout portion 22d is fitted into a recessed portion 11b11 of the rib 11b1 of the first grip case 10A, and a hook 11b12 of the rib 11b1 and an inner surface of the engaging portion 11k press both surfaces of the engaging portion 21 of the head case 20; thus, the rib 11b1 and the cutout portion 22d are engaged. The other five ribs and the other five cutout portions are similar.

Figure 10:
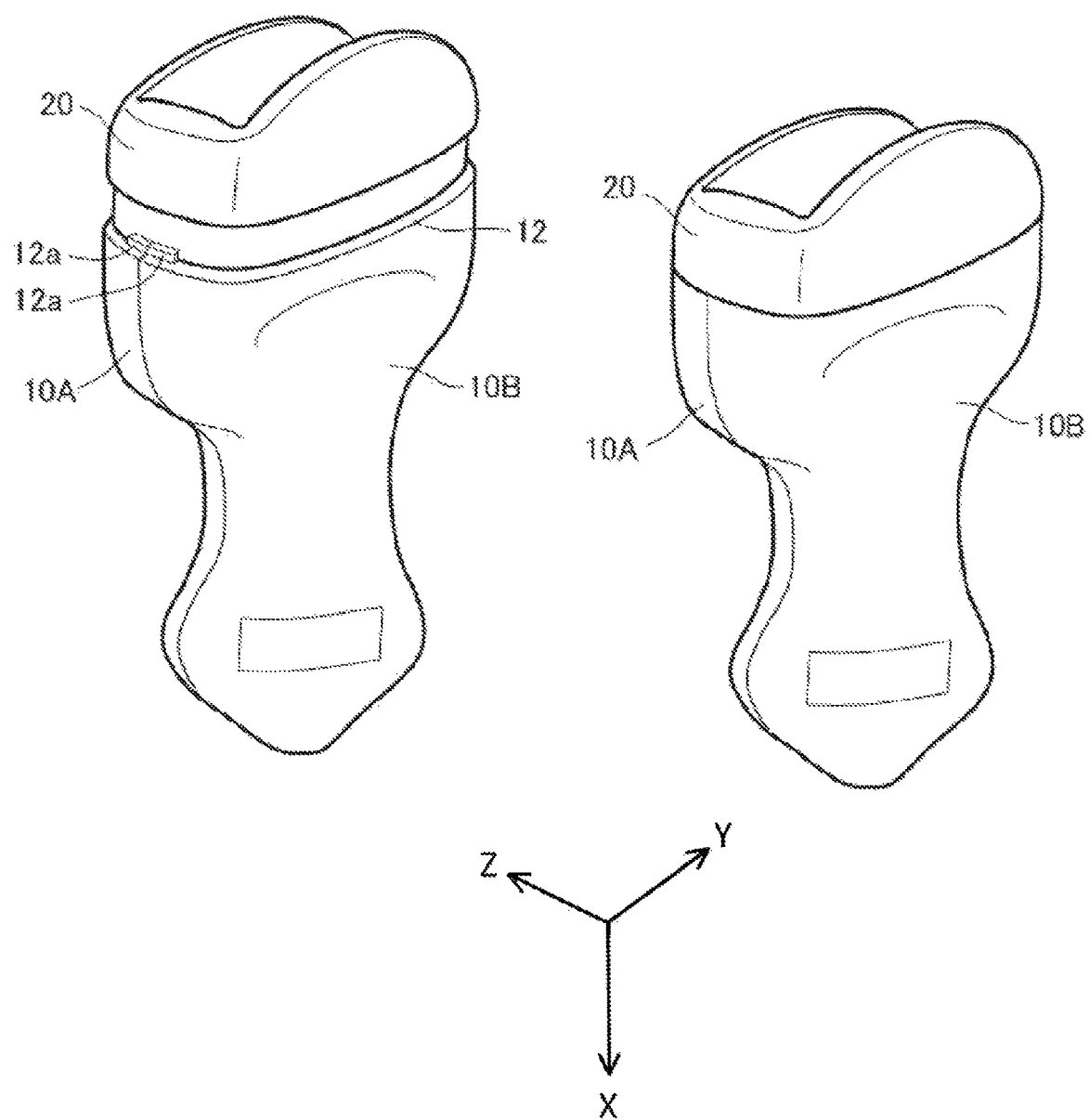
FIG. 10 is a drawing illustrating a state immediately before the grip case and the head case are mounted and a state where the grip case and the head case are mounted.

FIG. 10 is a drawing illustrating a state immediately before the grip case 10 and the head case 20 are mounted and a state where the grip case 10 and the head case 20 are mounted. As illustrated in FIG. 10, when the grip case 10 (the first grip case 10A and the second grip case 10B) and the head case 20 are engaged, the protrusions 12a of the grip case 10 are fitted into the grooves 24a and 24b of the head case 20 and then engaged. At this time, as illustrated in FIG. 8A, FIG. 8B, and FIG. 9, the six ribs and the six cutout portions are also engaged.

Thus, a plurality of the ribs and a plurality of the cutout portions each play a role of engaging and fixing the grip case 10 and the head case 20 while positioning the grip case 10 and the head case 20. This surely ensures connecting the cases with one another without an occurrence of a level difference between an outer surface of the grip case 10 and an outer surface of the head case 20. The plurality of ribs inside the grip case 10 enter the plurality of cutout portions of the head case 20 and are hooked, thus playing a role of a hook. Accordingly, once the grip case 10 and the head case 20 are engaged, the grip case 10 and the head case 20 are not peeled off even though they are pulled. The plurality of ribs also play a role of a reinforcement such that, for example, a depression of the case would not occur when the plurality of ribs engage with the respective plurality of cutout portions.

As described above, in this embodiment, an outer case that houses the module of the ultrasonic probe 1 includes the grip case 10 gripped by a user and the head case 20 that engages with the grip case 10. The engaging portion 11k of the grip case 10 includes one or the plurality of convex portions 11b1 to 11b6. The engaging portion 21 of the head case 20 includes one or the plurality of depressed portions 22a, 22b, 22c, 22d, 22e, and 22f at the positions where the plurality of depressed portions 22a, 22b, 22c, 22d, 22e, and 22f engage with one or the plurality of convex portions 11b1 to 11b6. The convex portions 11b1 to 11b6 and the depressed portions 22a, 22b, 22c, 22d, 22e, and 22f are engaged to be locked. Such a configuration ensures surely connecting the cases with one another without an occurrence of a level difference at a seam of the cases.

In this embodiment, the protrusions 12a are formed in both ends of the peripheral edge portion 12 of the grip case 10 and the grooves 24a and 24b that engage with the protrusions 12a are formed at the positions corresponding to the protrusions 12a in both ends of the peripheral edge portion 22 of the head case 20. Such a configuration ensures surely engaging both ends of the cases and ensures not causing a gap even though the cases are pulled.

In this embodiment, the convex portions 11b1 to 11b6 are formed in the center between both ends of the peripheral edge portion 12 of the grip case 10 or the proximity of the center. Such a configuration ensures fixing the center or a portion in the proximity of the center (a middle between both ends of the case, that is, a position where the level difference easily occurs), which is easily depressed, thereby ensuring surely preventing the level difference from occurring at a joint of the cases.

In this embodiment, the convex portions 11b1 to 11b6 are the flat plate-shaped members that vertically project from the surface of the engaging portion 11k, thereby ensuring causing the convex portions 11b1 to 11b6 to play a role of the ribs (members/parts orthogonally installed with respect to the surface) reinforcing a fixing strength of the surface of the case.

In this embodiment, the grip case 10 is configured by combining the two parts 10A and 10B. Such a configuration ensures easily inserting the base plate 40 equipped with a transmitting and receiving module inside the grip case 10. Accordingly, only by connecting the USB cable 30 to the ultrasonic probe 1 ensures transmitting and receiving data between the ultrasonic probe 1 and the information equipment, such as the computer, thereby improving a convenience of the operator.

While the disclosure has been described above with reference to the embodiment, the technical scope of the disclosure is not limited to the scope of the embodiment described above. A variety of variations or modifications can be made for the above-described embodiment within a range not departing a gist of the disclosure. One or more requirements described in the above-described embodiment may be omitted. Such variations, modifications, or omitted embodiments are also encompassed by the technical scope of the disclosure. The above-described embodiment and modification configuration can also be appropriately combined and applied.

For example, while the above-described embodiment exemplarily described the convex type ultrasonic probe 1, it is not limited to such a probe and may be a probe of a linear type, a sector type, a single type, or the like.

In addition to being fixed only by the engagement of the convex portion and the depressed portion, the grip case 10 and the head case 20 may further be fixed (fixedly secured) using, for example, an adhesive.

The disclosure may be configured such that the grip case has an opening that has a first peripheral edge portion whose both ends include protrusions, and the head case has an opening that has a second peripheral edge portion whose both ends include grooves that engage with the protrusions at positions corresponding to the protrusions.

The disclosure may be configured such that the convex portion is disposed in a center between both ends of a first peripheral edge portion in an opening of the grip case or in a proximity of the center.

The disclosure may be configured such that the convex portion is a flat plate-shaped member vertically projecting from a surface of the first engaging portion.

The disclosure may be configured such that the grip case is configured by combining two parts.

With the disclosure, the grip case and the head case can be engaged while the convex portion and the depressed portion are positioned by the engagement, thereby no level difference occurring at a seam of the cases. The engagement of the convex portion and the depressed portion reinforces the engagement of the grip case and the head case, thereby ensuring surely preventing of the cases from being displaced or peeled off.

The principles, preferred embodiment and mode of operation of the present invention have been described in the foregoing specification. However, the invention which is intended to be protected is not to be construed as limited to the particular embodiments disclosed. Further, the embodiments described herein are to be regarded as illustrative rather than restrictive. Variations and changes may be made by others, and equivalents employed, without departing from the spirit of the present invention. Accordingly, it is expressly intended that all such variations, changes and equivalents which fall within the spirit and scope of the present invention as defined in the claims, be embraced thereby.

What is claimed is:

1. An outer case for an ultrasonic probe that houses a module of the ultrasonic probe, the outer case comprising:
   a grip case, being gripped by a user; and
   a head case that engages with the grip case;
   wherein the grip case has a first engaging portion where one or a plurality of convex portions are disposed,
   the head case has a second engaging portion where one or a plurality of depressed portions are disposed at positions where the one or plurality of depressed portions engage with the one or plurality of convex portions, and
   the convex portion and the depressed portion are engaged to be locked.

2. The outer case for an ultrasonic probe according to claim 1, wherein
   the grip case has a first peripheral edge portion whose both ends include protrusions, and
   the head case has a second peripheral edge portion whose both ends include grooves that engage with the protrusions at positions corresponding to the protrusions.

3. The outer case for an ultrasonic probe according to claim 1, wherein
   the convex portion is disposed in a center between both ends of a first peripheral edge portion of the grip case or in a proximity of the center.

4. The outer case for an ultrasonic probe according to claim 1, wherein
   the convex portion is a flat plate-shaped member vertically projecting from a surface of the first engaging portion.

5. The outer case for an ultrasonic probe according to claim 1, wherein
   the grip case is configured by combining two parts.

* * * * *